United States Patent
Blau et al.

(10) Patent No.: US 7,481,761 B2
(45) Date of Patent: *Jan. 27, 2009

(54) IMPLANTABLE CONVERTER FOR COCHLEA IMPLANTS AND IMPLANTABLE HEARING AIDS

(75) Inventors: Matthias Blau, Dresden (DE); Matthias Bornitz, Dresden (DE); Thomas Zahnert, Dresden (DE); Gert Hofmann, Langebrück (DE); Karl-Bernd Hüttenbrink, Dresden (DE)

(73) Assignee: Med-El Elektromedizinische Geräte Ges.m.b.H., Innsbruck (AT)

( * ) Notice: Subject to any disclaimer, the term of this patent is extended or adjusted under 35 U.S.C. 154(b) by 503 days.

This patent is subject to a terminal disclaimer.

(21) Appl. No.: 10/757,355

(22) Filed: Jan. 14, 2004

(65) Prior Publication Data

US 2005/0113633 A1 May 26, 2005

(30) Foreign Application Priority Data

Jan. 15, 2003 (DE) ............ 103 01 723

(51) Int. Cl.
H04R 25/00 (2006.01)
(52) U.S. Cl. ............ 600/25
(58) Field of Classification Search ........ 600/9–15, 600/29–32, 25; 623/14.13; 604/96.01; 128/897–899; 607/56–59; 381/312–320
See application file for complete search history.

(56) References Cited

U.S. PATENT DOCUMENTS

| 554,096 | A | 2/1896 | Strouse |
| 3,712,962 | A | 1/1973 | Epley |
| 3,870,832 | A | 3/1975 | Fredrickson |
| 3,882,285 | A | 5/1975 | Nunley et al. |
| 4,988,333 | A | 1/1991 | Engebretson et al. |
| 5,411,467 | A | 5/1995 | Hortmann et al. |
| 5,558,618 | A * | 9/1996 | Maniglia ............ 600/25 |
| 5,836,863 | A * | 11/1998 | Bushek et al. ............ 600/25 |
| 6,422,991 | B1 * | 7/2002 | Jaeger ............ 600/25 |
| 6,627,104 | B1 * | 9/2003 | Wang et al. ............ 252/62.9 PZ |
| 2001/0003788 | A1 * | 6/2001 | Ball et al. ............ 600/25 |
| 2002/0019669 | A1 * | 2/2002 | Berrang et al. ............ 623/10 |
| 2005/0137447 | A1 * | 6/2005 | Bernhard ............ 600/25 |

FOREIGN PATENT DOCUMENTS

DE 19858398 C1 3/2000

(Continued)

Primary Examiner—Samuel G Gilbert
(74) Attorney, Agent, or Firm—Henry M. Feiereisen; Ursula B. Day

(57) ABSTRACT

The invention relates to an implantable electromechanical converter for receiving oscillations from an ear ossicle and for converting them into an electrical voltage, for use as a microphone for a cochlea implant or an implantable hearing aid, consisting of one or more piezoelectric converter elements (11) housed in a hermetically sealed hollow body (2) made of a biocompatible material. The converter is characterized in that the hollow body has a thin shell (9) which is connected with its interior side to the piezoelectric converter elements and which can be coupled with its exterior side to an ear ossicle, and which is held by a stable edge (10), whereby the stable edge can be coupled to a counter-support in the middle ear space.

21 Claims, 5 Drawing Sheets

FOREIGN PATENT DOCUMENTS

| | | |
|---|---|---|
| DE | 19858399 A1 | 7/2000 |
| DE | 10030372 C2 | 1/2002 |
| DE | 10163513 A1 | 7/2003 |
| EP | 0 263 254 B1 | 7/1992 |
| EP | 0 831 673 A2 | 3/1998 |
| WO | WO 94/17645 | 8/1994 |
| WO | WO 96/21333 | 7/1996 |
| WO | WO 97/18689 | 5/1997 |
| WO | WO 99/08480 | 2/1999 |

* cited by examiner

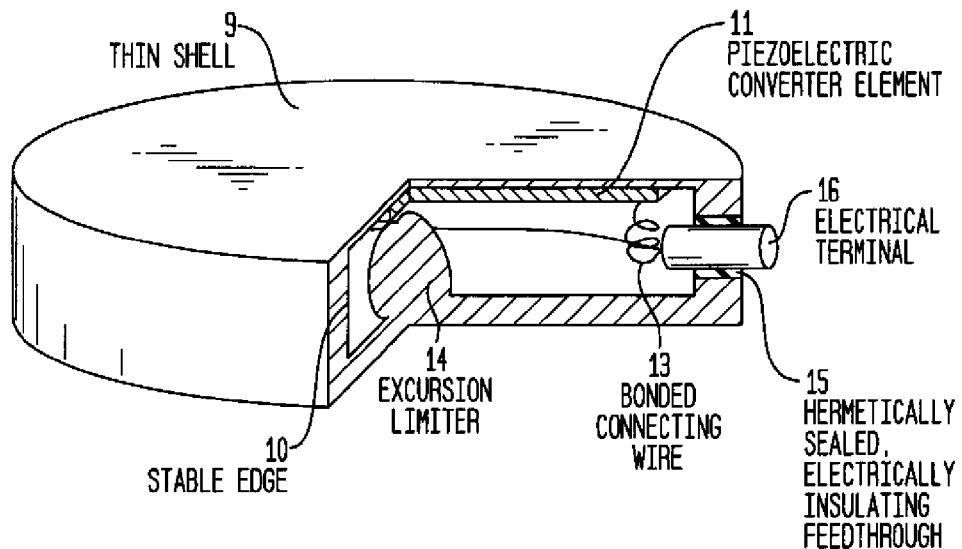
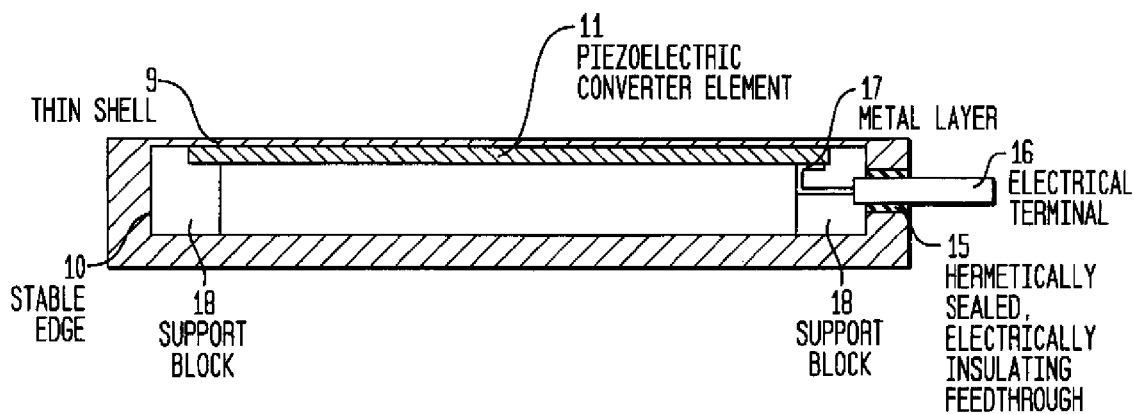

IMPLANTABLE CONVERTER FOR COCHLEA IMPLANTS AND IMPLANTABLE HEARING AIDS

BACKGROUND OF THE INVENTION

The invention relates to an implantable electromechanical converter for cochlea implants and for implantable hearing aids.

Completely or partially implantable hearing aids, such as cochlea implants or implantable hearing aids, require an implantable converter for receiving the sound reaching the ear of the patient, since the sound has to be converted into electrical signals for further processing in the respective hearing aid.

Different solutions have been proposed in the past. In a first approach, the sound waves reaching the ear are directly converted into electrical signals which can be accomplished in different ways, as described, for example, in U.S. Pat. Nos. 3,882,285, 4,988,333, WO 96/21333, U.S. Pat. No. 5,411,467, and EP 0 831 673. With this approach, however, the natural ability of the outer ear of directionally filtering the received sound is lost and/or the attachment/implantation of the required converter components can cause adverse reactions of the affected/surrounding tissue.

In a second approach, the natural sound receiving mechanisms of the human outer and middle ear are used for converting the received sound into oscillations of the middle ear components (eardrum and ear ossicle), which are subsequently converted into electrical signals. Different converter principles have been proposed: U.S. Pat. No. 3,870,832 describes implantable converters based on electromagnetic principles. However, the relatively high power consumption of such electromagnetic and electrodynamic converters limits their practical application for implantable cochlea implants and hearing aids.

This disadvantage is obviated by converters based on piezoelectric principles. EP 0 263 254 describes an implantable converter made of a piezoelectric film, a piezoelectric crystal or a piezoelectric acceleration sensor, whereby one end of the converter is cemented in the bone while the other end is fixedly connected with an oscillating member of the middle ear. The problem with this approach is that inflexible connections to the ear ossicles can cause bone erosion, so that cementing converter components in the middle ear space is approached cautiously for mechanical and toxicological reasons. Moreover, the patent reference does not indicate how the body fluids can be permanently prevented from making contact with the piezoelectric materials. Accordingly, there is a risk of biocompatibility problems, so that the piezoelectric properties can deteriorate due to physical and chemical interactions between the piezoelectric material and the body fluids.

U.S. Pat. No. 3,712,962 describes an implantable converter that uses a piezoelectric cylinder or a piezoelectric beam as a converter component that is anchored in the ear in a manner that is not described in detail. This reference, like the aforementioned patent EP 0 263 254, does not describe in detail how body fluids can be permanently prevented from making contact with the piezoelectric materials.

WO 99/08480 describes an implantable converter based on piezoelectric principles, which is attached solely to an oscillating middle ear component, with the counter support being provided by an inertial mass connected with the converter. However, the attachment of the converter to an oscillating middle ear component, such as the ear drum or the ear ossicles, is either not permanently stable or can erode the bone. This risk is aggravated because the mass of the implantable converter is greater than that of passive middle ear implants.

WO 94/17645 describes an implantable converter based on capacitive or a piezoelectric principles, that can be fabricated by micromechanical techniques. This converter is intended to operate a pressure detector in the incus-stapes joint. Since the stapes in conjunction with the coupled inner ear forms a resonant system, it may not have sufficient sensitivity across the entire range of useful frequencies. This problem applies also to the implantable converters described in WO 97/18689 and DE 100 30 372 that operate by way of hydro-acoustic signal transmission.

Based on the present state of the art, it is therefore an object to provide an improved implantable microphonic device that converts sound received by the ear into electrical signals with sufficient sensitivity over the entire useful frequency range, that consumes as little energy as possible, that protects the sensitive bone and tissue structures of the ear by suitable positioning and coupling of the implantable microphone, and that provides long-term stability and biocompatibility of the implantable microphonic device.

SUMMARY OF THE INVENTION

The object is solved by an implantable electromechanical converter for receiving oscillations from an ear ossicle and for converting the received oscillations into an electrical voltage, for use as a microphone for a cochlea implant or an implantable hearing aid, including piezoelectric converter elements housed in a hermetically sealed hollow body made of a biocompatible material, wherein the hollow body has a thin shell which is coupled on its interior side with piezoelectric converter elements and can be coupled on its exterior side to an ear ossicle, and is supported by a stable edge which is coupled to a counter-support in the middle ear space.

According to the invention, mechanical oscillations are converted into electrical voltage by one or several piezoelectric converter elements, which are surrounded by a hermetically sealed hollow body made of a biocompatible material, preferably titanium or a titanium alloy, to provide insulation against body fluids. The hollow body is constructed with a thin shell which is supported by a stable edge, which can be coupled to a counter-support in the middle ear space.

On the inside of the hollow body, the piezoelectric converter elements are connected with the thin shell. The outside of the thin shell is coupled to the ear ossicles, so that the oscillations of the ear ossicles cause deformation of the piezoelectric converter elements and hence induce an electrical voltage at the electrodes of the converter elements.

Electrical voltage is routed via hermetically sealed, electrically insulating feedthroughs (made, for example, of glass, precious or semiprecious stones) to corresponding terminals located outside the hollow body. The electric voltage can then be further processed in a cochlea implant or a hearing aid.

By coupling the device to one of the ear ossicles across a larger area, damage to the bone structures can be essentially prevented.

According to an advantageous embodiment of the converter, the hollow body is formed as an elliptical cup, whereby a piezoelectric converter element in the form of a thin bending plate is connected with the thin shell which is formed as a thin elliptical plate. With this configuration, the height of the cup can be reduced to less than 1 mm.

The stable edge and the thin shell can be connected by different joining methods, for example welding. The stable edge and the thin shell can also be fabricated as one piece, for example, by using mechanical separation and forming methods or by chemical methods, such as etching.

The piezoelectric converter elements can also be connected to the thin shell with adhesive or by other mechanical means. The piezoelectric converter elements themselves can be made of any conventional piezoelectric material. Advantageously, single crystals made of lead magnesium niobate-lead titanate (PMN-PT) or lead zinc niobate-lead titanate (PZN-PT) can be used, which due to their electromechanical properties allow a significant reduction in the physical size of the piezoelectric converter elements and hence the size of the entire converter unit.

Moreover, the hollow body can include an electronic signal conditioning circuit to reduce interferences in the signal voltage at the outer electrical terminals.

The counter-support can be implemented in several ways. In one embodiment, a support element is fabricated of a biocompatible material, preferably titanium or a titanium alloy, which is placed near the recess of the oval window and adapted to receive the hollow body. Alternatively, a support element can be screwed into a bone of the middle ear space. In both embodiments, adhesives can be eliminated which reduces the risk of toxicological damage.

BRIEF DESCRIPTION OF THE DRAWING

The invention will be described hereinafter with reference to exemplified embodiments. The drawings show in:

FIG. 3 an embodiment of the converter that is positioned by spacer plates;

FIG. 4 an embodiment of a hollow body with piezoelectric converter elements joined by an adhesive;

DETAILED DESCRIPTION OF PREFERRED EMBODIMENTS

Figure 1:
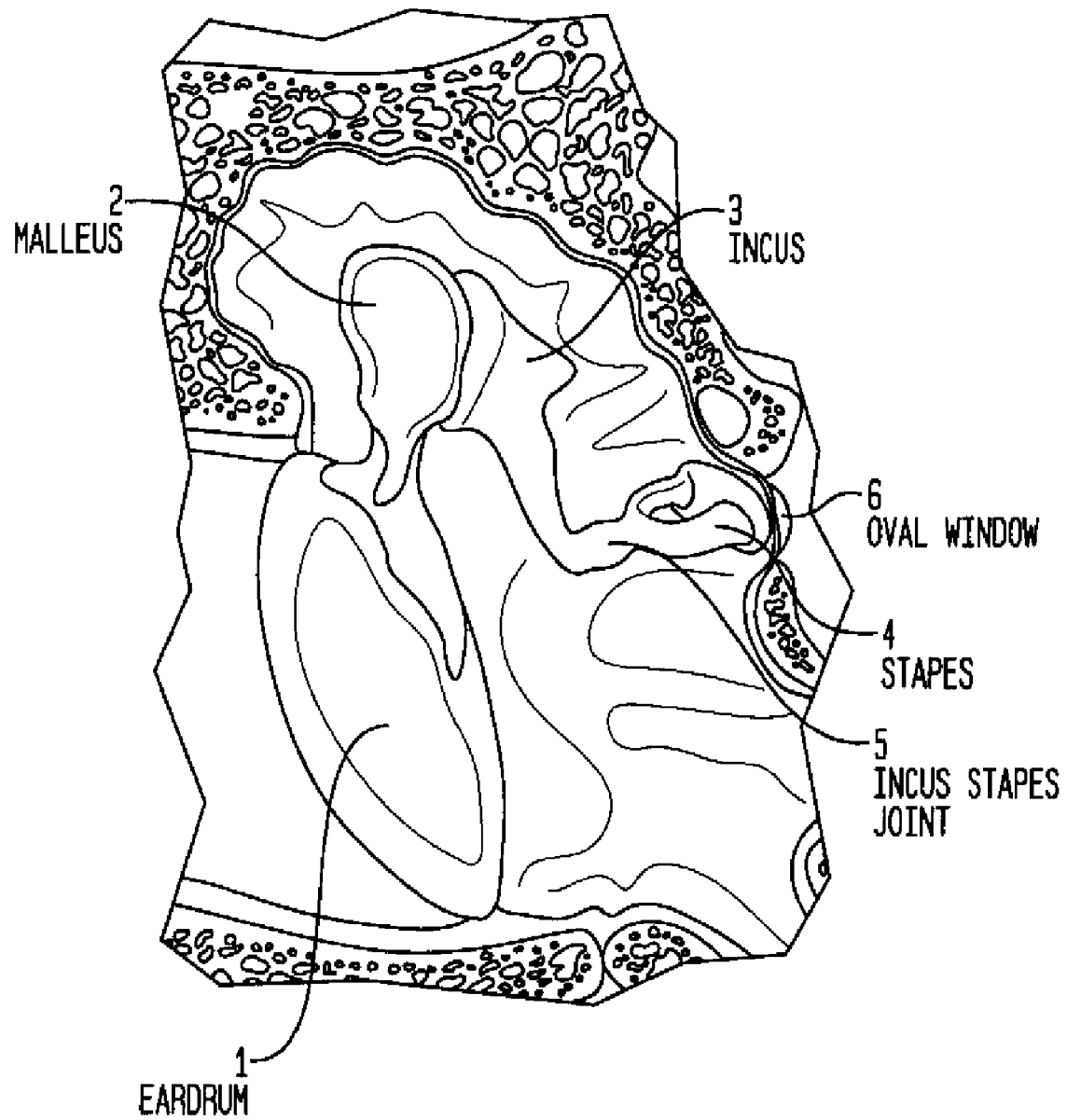
FIG. 1 an overview over the relevant structures of the middle ear space.

FIG. 1 is a schematic overview of relevant structures of the middle ear space. Sound waves reach the eardrum 1 and excite oscillations which are transmitted to the oval window 6 of the inner ear through the ear ossicles, i.e., the malleus 2, the incus 3 and the stapes 4. Also shown is the incus-stapes joint 5.

Figure 2:
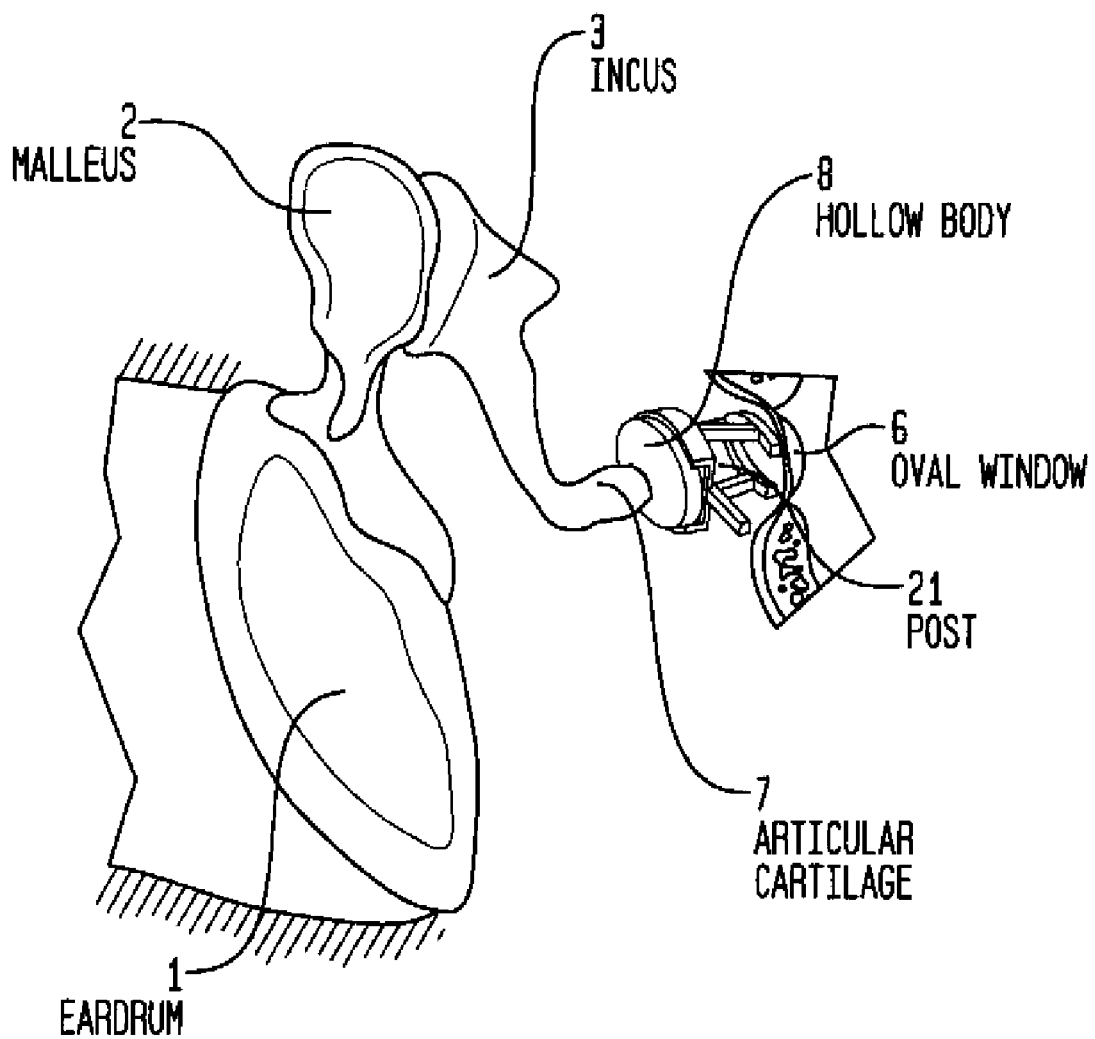
FIG. 2 a cross-section of the middle ear space with one embodiment of the implanted converter.

FIG. 2 shows a cross-section of the middle ear region with an embodiment of the implanted converter operating as a microphone for a cochlea implant. In this embodiment, the hollow body 8 is made of a flat elliptical cup which is connected on one side with the articular cartilage 7 of the severed malleus-incus joint 5 and on the other side with a post 21 located in the recess of the oval window 6 and affixed in the bone channel of the stapes tendon. The oscillations of the ear drum 1 are transmitted from the malleus 2, incus 3 and articular cartilage 7 to the thin shell of the hollow body 8. The risk of damaging the bone tissue of the incus 3 is minimized due to the contact via the articular cartilage.

Figure 6:
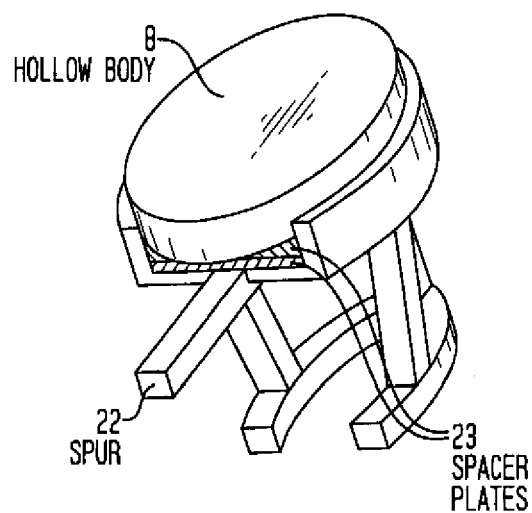
FIG. 6 an embodiment of a hollow body with an electronic signal conditioning circuit.

FIG. 6 illustrates more closely the embodiment of the converter depicted in FIG. 2. The hollow body 8 includes an elliptical plate-like thin shell and a stable edge that is shaped into an elliptical hollow cylinder with a bottom. The stable edge of the hollow body 8 is connected with the support element via spacer plates 23, whereby the support element has a spur 22 as an anchoring means in the bone channel of the stapes tendon. FIG. 3 shows an embodiment of the hollow body and the structures housed in the hollow body. The hollow body is here fabricated of an elliptical plate-shaped thin shell 9 and a stable edge 10 made of titanium or a titanium alloy that are shaped into an elliptical hollow cylinder with a bottom. A plate-shaped piezoelectric converter element 11 is affixed to the thin shell 9 with an adhesive so as to be electrically conducting. The electric voltage relative to the hollow titanium body is supplied to an electric terminal 16 via a bonded connecting wire 13. The electric terminal 16 is connected with the stable edge 10 by a hermetically sealed, electrically conducting feedthrough 15. An excursion limiter 14 can be employed to limit the maximum excursion and thus prevent a high mechanical load on the thin shell 9.

FIG. 4 shows another embodiment of the hollow body is well as the structures housed in the hollow body. The thin shell 9 and the stable edge 10 are again made of titanium or a titanium alloy. The piezoelectric converter element 11 is here supported by support blocks 18. The piezoelectric converter element can be readily contacted by a metal layer 17 applied to one or both support blocks. The metal layer 17 is connected with the electric terminal 16, which is again connected with the stable edge 10 via a hermetically sealed, electrically conducting feedthrough 15.

Figure 5:
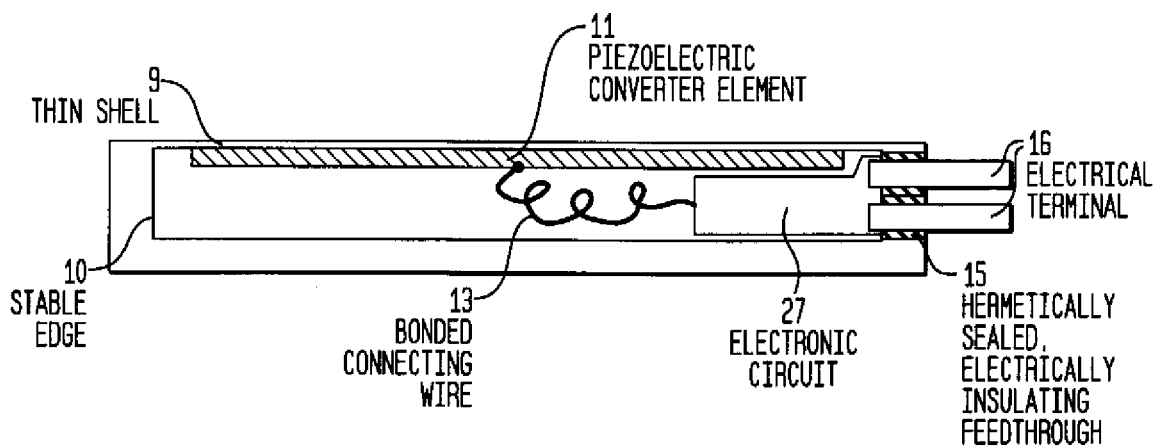
FIG. 5 an embodiment of a hollow body with mechanically supported piezoelectric converter elements.

FIG. 5 shows another embodiment of the hollow body as well as the structures housed in the hollow body. The thin shell 9 and the stable edge 10 are made of titanium or a titanium alloy, and a plate-shaped piezoelectric converter element 11 is affixed to the thin shell 9 with an adhesive so as to be electrically conducting. The electric voltage relative to the hollow titanium body is routed via a bonded connecting wire 13 to an electronic circuit 27 which conditions the signal voltage. Since an operating voltage has to be applied to the circuit 27 to provide electric power, two electric terminals 16 are provided which are connected with the stable edge 10 via hermetically sealed, electrically insulating feedthroughs 15.

Figure 7:
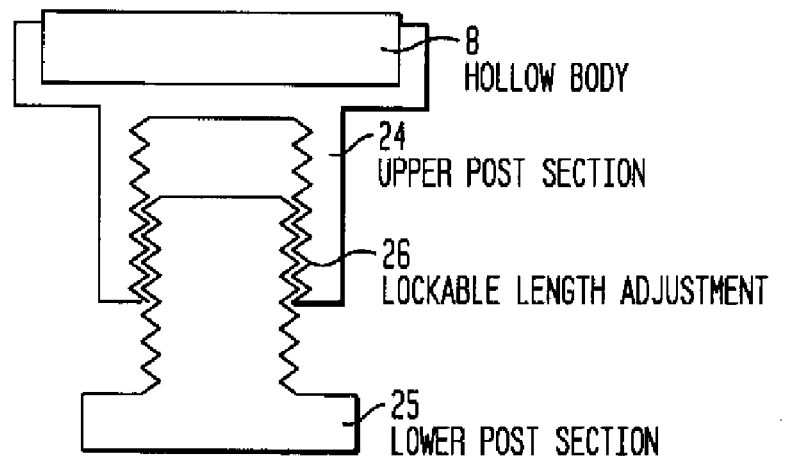
FIG. 7 an embodiment of the converter with a lockable two-part support element.

FIG. 7 shows an embodiment of the converter, where the counter-support is formed by a support element that can be supported in the recess of the oval window. The position of the hollow body 8 can be adjusted by constructing the post of an upper post section 24 and a lower post section 25 that are connected with each by a lockable length adjustment element 26.

Figure 8:
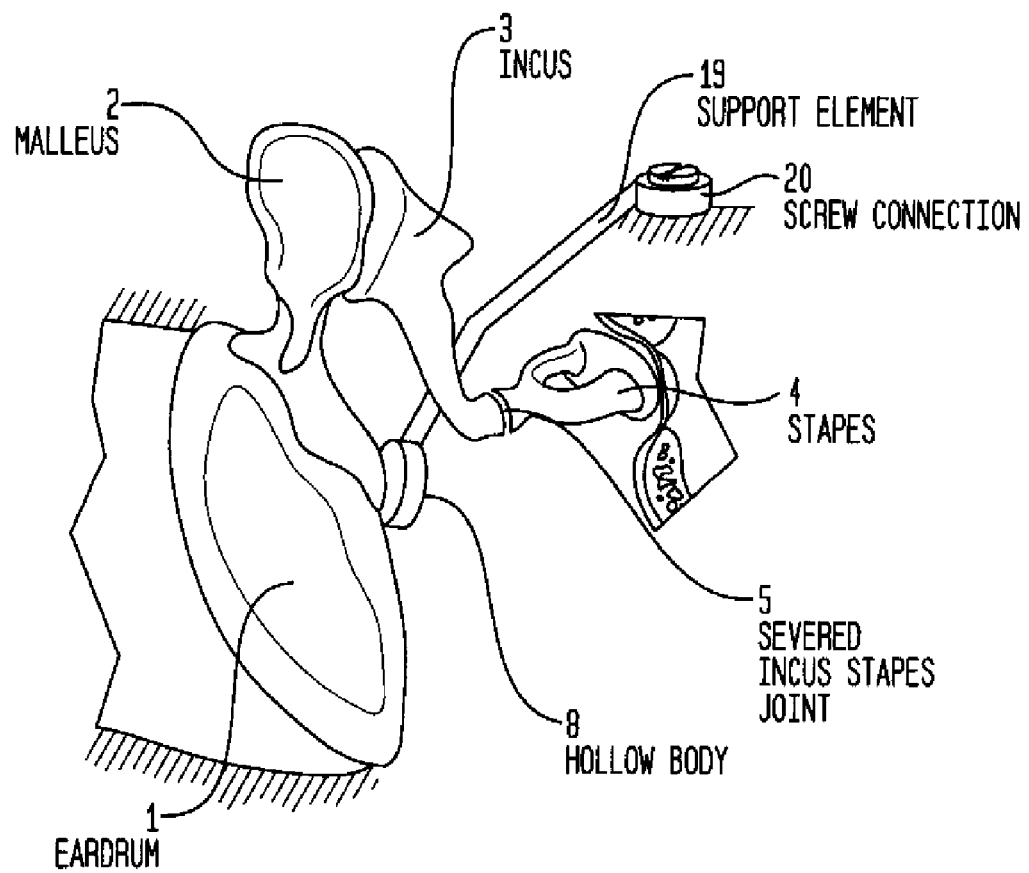
FIG. 8 a cross-section of the middle ear space with an additional embodiment of the implanted converter.

FIG. 8 shows a cross-section of the middle ear region with a different embodiment of the implanted converter of the invention operating as a microphone for an implantable hearing aid. In this embodiment, the hollow body 8 has again the form of a flat elliptical cup that is coupled to the malleus 2. The counter support is here implemented as a support element 19 that is connected to the stable edge of the cup and extends to a screw connection 20 with an ossicle of the middle ear space. The incus-stapes joint 5 is severed in order to prevent feedback of oscillations to the implanted converter from the inner ear fluid that is in fluid connection with the stapes 4. The oscillations of the eardrum 1 are transmitted to the malleus 2, the incus 3, and the thin shell of the hollow body 8.

What is claimed is:

1. An implantable electromechanical converter for receiving oscillations from an ear ossicle and for converting the received oscillations into an electrical voltage, for use as a microphone for a cochlea implant or an implantable hearing aid, comprising:

a hermetically sealed hollow body made of a biocompatible material, said hollow body having a thin shell with an exterior side adapted to be coupled to the ear ossicle and an interior side;

an electronic circuit for conditioning the electrical voltage located inside the hollow body, and a stable edge supporting the thin shell, said stable edge being coupled to a counter-support in the middle ear space, wherein the electromechanical converter is implemented as at least one piezoelectric converter element housed in the hollow body and coupled the interior side of the thin shell.

2. The converter of claim 1, wherein the stable edge is shaped as an elliptical hollow cylinder.

3. The converter of claim 1, wherein the hollow body includes a means for limiting an excursion of the thin shell.

4. The converter of claim 1, wherein the biocompatible material of the hollow body comprises titanium or a titanium alloy.

5. The converter of claim 1, wherein the thin shell is formed as a plate with a thickness of between 20 and 50 μm.

6. The converter of claim 1, wherein a connection between the thin shell and the stable edge is welded.

7. The converter of claim 1, wherein the thin shell and the stable edge are formed as a single piece and are shaped by a mechanical separation or forming process or an etching process.

8. The converter of claim 1, wherein the at least one piezoelectric converter element comprises an element selected from the group consisting of a piezoelectric ceramic material, a piezoelectric film, and a piezoelectric single crystal.

9. The converter of claim 8, wherein the element comprises lead zinc niobate-lead titanate (PZN-PT) or lead magnesium niobate-lead titanate (PMN-PT).

10. The converter of claim 1, wherein the at least one piezoelectric converter element is connected with the thin shell by an adhesive.

11. The converter of claim 1, wherein the at least one piezoelectric converter element is mechanically supported on the interior side of the thin shell.

12. The converter of claim 1, and further comprising a hermetically sealed, electrically insulating feedthrough extending through the stable edge for providing an external connection to the electrical voltage.

13. The converter of claim 1, wherein the at least one piezoelectric converter element is implemented as unimorphic or multimorphic bending plate or bending beam.

14. The converter of claim 12, wherein the feedthrough is made of a material selected from the group consisting of glass, ceramics and minerals.

15. The converter of claim 1, wherein the thin shell is adapted to be coupled to the articular cartilage of the severed incus-stapes joint that is coupled with the long incus appendage.

16. The converter of claim 1, and further comprising a post having two ends and made of a biocompatible material, said post forming a counter-support which is adapted to be supported on a first of the two ends in a recess of the oval window of the inner ear and is configured on the other end to receive the stable edge.

17. The converter of claim 16, wherein the post includes a means for anchoring the post in a bone canal of the stapes tendon.

18. The converter of claim 16, wherein the post includes positioning means for positioning the thin shell relative to the coupled ear ossicle.

19. The converter of claim 18, wherein the positioning means are implemented as insertable support plates or wedges made of a biocompatible material which are inserted between the post and the stable edge.

20. The converter of claim 18, wherein the post comprises two segments that are adapted to be lockably engaged.

21. The converter of claim 1, wherein the counter-support is implemented as a support element having two ends, with one end being connected with the stable edge and the other end adapted to connect with a bone by a screw connection.

* * * * *